US012139761B2

(12) United States Patent
Gysemans et al.

(10) Patent No.: US 12,139,761 B2
(45) Date of Patent: Nov. 12, 2024

(54) BIOMARKERS FOR DIABETES THERAPY

(71) Applicants: KATHOLIEKE UNIVERSITEIT LEUVEN, Leuven (BE); UNIVERSITÀ DI SIENA, Siena (IT)

(72) Inventors: Constantia Gysemans, Rostelaar (BE); Chantal Mathieu, Buizingen (BE); Francesco Dotta, Rome (IT); Guido Sebastiani, Siena (IT); Giuliana Ventriglia, Caserta (IT)

(73) Assignees: KATHOLIEKE UNIVERSITEIT LEUVEN, Leuven (BE); UNIVERSITÀ DI SIENA, Siena (IT)

( * ) Notice: Subject to any disclaimer, the term of this patent is extended or adjusted under 35 U.S.C. 154(b) by 1069 days.

(21) Appl. No.: 17/043,136

(22) PCT Filed: Mar. 29, 2019

(86) PCT No.: PCT/EP2019/058001
§ 371 (c)(1),
(2) Date: Sep. 29, 2020

(87) PCT Pub. No.: WO2019/185864
PCT Pub. Date: Oct. 3, 2019

(65) Prior Publication Data
US 2021/0371927 A1    Dec. 2, 2021

(30) Foreign Application Priority Data
Mar. 30, 2018  (GB) ...................................... 1805329

(51) Int. Cl.
*C12Q 1/6883* (2018.01)
(52) U.S. Cl.
CPC ..... *C12Q 1/6883* (2013.01); *C12Q 2600/106* (2013.01); *C12Q 2600/158* (2013.01); *C12Q 2600/178* (2013.01)
(58) Field of Classification Search
CPC ............ C12Q 1/6883; C12Q 2600/178; C12Q 2600/158; C12Q 2600/106
See application file for complete search history.

(56) References Cited

FOREIGN PATENT DOCUMENTS

JP    2013188208 A    9/2013

OTHER PUBLICATIONS

Negrini et al., "microRNAome expression in chronic lymphocytic leukemia comparison with normal B cell subsets and correlations with prognostic and clinical parameters," Clinical Cancer Research, on-line publication Jun. 10, pp. 1-24 (print out). (Year: 2014).*
Okuda et al., "Frequent Deletion of p16(INK4a)/MTS1 and p15(INK4b/MTS2 in Pediatric Acute Lymphoblastic Leukemia," Blood, May 1, vol. 85, No. 9, pp. 2321-2330 (Year: 1995).*
Lucentini et al., "Gene Association Studies Typically Wrong," The Scientist, Dec. 20, vol. 18, No. 24, print-out pp. 1-4. ( Year: 2004).*
Wacholder et al., "Assessing the Probability That a Positive Report is False: An Approach for Molecular Epidemiology Studies," Journal of National Cancer Institute, Mar. 17, vol. 96, No. 6, pp. 434-442. (Year: 2004).*
Ioannidis et al., "Replication validity of genetic association studies," Nature Genetics, November, vol. 29, pp. 306-309. (Year: 2001).*
International Search Report in reference to co-pending European Patent Application No. PCT/EP2019/058001 filed Mar. 29, 2019.
Written Opinion in reference to co-pending European Patent Application No. PCT/EP2019/058001 filed Mar. 29, 2019.
Atkinson, et al., "Type 1 diabetes", Seminar CrossMark, vol. 383, pp. 69-82, Jan. 4, 2014.
Cook, et al., "Lactococcus lactis As a Versatile Vehicle for Tolergenic Immunotherapy", Frontiers in Immunology, vol. 3, Article 1961, pp. 1-16, Jan. 2018.
Livak, et al., "Analysis of Relative Gene Expression Data Using Real-time Quantitative PCR and the 2(-Delta Delta C (T)) Method", Methods, vol. 25, pp. 402-408, 2011.
Roep, et al., Immune modulation in humans: implications for type 1 diabetes mellitus, Nature Reviews, Endocrinology, vol. 10, pp. 229-242, Apr. 2014.
Samandari, et al., "Circulating microRNA levels predict residual beta cell function and glycaemic control in children with type 1 diabetes mellitus", Diabetologia Article, CrossMark, vol. 60, pp. 354-363, 2017.
Seyhan, et al., "Pancreas-enriched miRNAs are altered in the circulation of subjects with diabetes:a pilot cross-sectional study", Scientific Reports, pp. 1-15, 2016.
Takiishi, et al., Reversal of autoimmune diabetes by restoration of antigen-specific tolerance using genetically modified Lactococcus lactis in mice, Research Article, vol. 122, No. 5, pp. 1717-1725, May 2012.
Takiishi, et al., "Reversal of Diabetes in NOD Mice by Clinical-Grade Proinsulin and IL-10-Secreting Lactococcus lactis in Combination With Low-Dose Anti-CD3 Depends on the Induction of Foxp3-Positive T Cells", Diabetes, vol. 66, pp. 448-459, Feb. 2017.
Kosaka, et al., Functional Analysis of Exosomal MicroRNA in Cell-Cell Communication Research, Methods in Molecular Biology, vol. 124, pp. 1-270, 2013.

\* cited by examiner

*Primary Examiner* — Young J Kim
(74) *Attorney, Agent, or Firm* — Dinsmore & Shohl LLP

(57) ABSTRACT

The invention relates to an in-vitro method for identifying a diabetic patient as responder or non-responder to a treatment of Proinsulin, Interleukin 10 and anti-CD3, based on the expression level of at least 1 microRNA, selected from the group consisting of miR-365, miR-34a, miR-193b and miR-125a, in a sample from the diabetic patient prior to said treatment.

14 Claims, 4 Drawing Sheets

Specification includes a Sequence Listing.

BIOMARKERS FOR DIABETES THERAPY

CROSS-REFERENCES TO RELATED APPLICATIONS

This application is a national-stage entry under 35 U.S.C. § 371 of International Application No. PCT/EP2019/058001, filed Mar. 29, 2019, which claims benefit of priority to Great Britain Patent Application No. 1805329.8, filed Mar. 30, 2018.

BACKGROUND

Type 1 diabetes (T1D) is an autoimmune disease that results from T cell-mediated destruction due to breach in immune tolerance toward insulin producing β-cells, leading to an absolute insulin deficiency [Atkinson et al. (2014) *The Lancet*. 383, 69-82]. Immune tolerance-restoration strategies have long been thought to be the key to arrest or prevent β-cell destruction [Roep & Tree (2014) *Nat Rev Endocrinol*. 10, 229-242]. However, although prevention strategies aimed at reprogramming the immune system toward tolerance before the onset of autoimmune diabetes in non-obese diabetic (NOD) mice were successful, those aimed at arresting ongoing β-cell destruction after onset were not.

A combination therapy consisting of a 5-day course of anti-CD3 antibodies at disease onset along with a 6-week oral administration of live genetically-modified *Lactococcus lactis* (*L. lactis*) producing human pro-insulin (PINS) and interleukin (IL10), restored durable normoglycemia in approximately 60% of NOD mice and elicited forkhead box p3 (Foxp3)-positive T cells with a regulatory phenotype [Takiishi et al. (2012) *J. Clin Invest*. 122, 1717-1725; Takiishi et al. (2017) Diabetes. 66, 448-459]. Even though *L. Lactis* therapy was successful in the reversal of autoimmune diabetes in 60% of NOD-mice, 40% did not respond to therapy. The route to bring this successful antigen-based therapy from preclinical model to clinics will depend on both safety of a clinical-grade self-containing *L. lactis* and the implementation of certified biomarkers of therapeutic success.

Recently, microRNAs, a class of small non-coding RNAs of 19-24 nucleotides long, have been proposed as blood-circulating biomarkers. Samandari et al. (2017) *Diabetologia* 60, 354-363 disclose miRNAs as predictor of residual beta cell function 1 year after diagnosis in children with type 1 diabetes mellitus. Seyhan et al. (2016) *Sci Rep*. 6, 31479 disclose that miRNAs linked to β-cell injury and islet inflammation might be useful biomarkers to distinguish between subtypes of diabetes.

There is a further need for reliable markers to evaluate whether patients will respond or not to newly developed therapies.

SUMMARY

The invention is summarized in the following statements:
1. An in-vitro method for identifying a diabetic patient as responder or non-responder to a treatment of Proinsulin, Interleukin 10 and anti-CD3, comprising the steps of:
   (a) determining the expression level of at least 1 microRNA, selected from the group consisting of miR-365, miR-34a, miR-193b and miR-125a, in a sample from the diabetic patient prior to said treatment, and
   (b) comparing the expression as determined in (a) with a control miRNA,
   wherein a decrease in the expression level of said at least one miRNA in the sample compared to a control miRNA is indicative for a response to said therapy.
2. The method according to statement 1, wherein the at least one microRNA is miR-193b or miR-365.
3. The method according to statement 2, wherein step (a) comprises determining the expression level of at least 2 microRNA selected from the group consisting of miR-365, miR-34a, miR-193b and miR-125a.
4. The method according to statement 1, wherein the at least two microRNA are miR-125a and one of miR-365 and miR-193b.
5. The method according to statement 4, wherein the at least two microRNA are miR-365 and miR-193b.
6. The method according to statement 1, wherein step a comprises determining the level of at least 3 microRNAs selected from the group consisting of miR-365, miR-34a miR-193b or miR-125a.
7. The method according to statement 6, wherein the at least 3 microRNA are miR-365 and miR-193b and one of miR-125a or miR-34a.
8. The method according to any one of statements 1 to 7, wherein the therapy comprises the oral administration of a micro-organism expressing Proinsulin and Interleukin 10.
9. In vitro use of one or more oligonucleotide probes specific for the detection of at least one microRNA selected from the group consisting of miR-365, miR-34a miR-193b and miR-125a, in the prediction of the response to a IL-10, proinsulin and CD3 antagonist therapy in a diabetic patient.
10. The use according to statement 9, wherein the at least one microRNA is miR-193b or miR-365.
11. The use according to statement 9 of oligonucleotide probes specific for the detection of at least two microRNA least 2 microRNA selected from the group consisting of miR-365, miR-34a, miR-193b and miR-125a.
12. The use according to statement 11, wherein the at least two microRNA are miR-125a and one of miR-365 and miR-193b.
13. The use according to statement 12, wherein the at least two microRNA are miR-365 and miR-193b.
14. The use according to statement 9 of oligonucleotide probes specific for the detection of at least 3 microRNAs selected from the group consisting of miR-365, miR-34a miR-193b or miR-125a.
15. The use according to statement 14, wherein the at least 3 microRNA are miR-365 and miR-193b and one of miR-125a or miR-34a.
16. A kit comprising oligonucleotide probes specific for the detection of at least two microRNA selected from the group consisting of miR-365, miR-34a miR-193b and miR-125a.
17. The kit according to statement 16, wherein the at least two micro-RNA are miR-193b and miR-365.
18. The kit according to statement 16 or 017, wherein the at least two micro-RNA are miR-193b and miR-365, and one of miR-34a or miR-125a
19. The kit according to any of statements 16 to 18, wherein said oligonucleotide probes are specific for the detection of cDNAs obtained from said microRNAs.
20. The kit according to any one of statements 16 to 19, adapted for performance of a quantitative reverse-transcription real-time polymerase chain reaction (qRT-PCR).
21. An in vitro method for identifying a type 1 diabetic patient as responder or non-responder to a treatment of Proinsulin or insulin, and Interleukin 10 and a CD3 antagonist, comprising the steps of, (a) determining the expression level of at least 1 microRNA, selected from the group consisting of miR-365, miR-34a, miR-193b and miR-125a, in a sample from the diabetic patient prior to said treatment, (b) comparing the expression level as determined in (a) with a control, (c) determining from said comparison, whether said patient is a responder or non-responder to said therapy.

22. The method according to statement 21, wherein expression levels are normalized against the expression of one or more control miRNA.

23. The method according to statement 21 or 22, wherein the control is one more endogenous miRNA.

24. The method according to any one of statements 21 to 23, wherein a high expression level of said at least one miRNA in the sample compared to the one or more control miRNA is indicative for non-responder to said therapy, and/or wherein a low expression level of said at least one miRNA in the sample compared to the one or more control miRNA is indicative for a responder to said therapy.

25. The method according to statement 21 or 22, wherein the control is the expression level of said at least one miRNA in one or more responder control persons, and wherein an increased expression compared to said control is indicative for a non-responder patient.

26. The method according to any one of statements 21 to 26, wherein the CD-3 antagonist is an antibody against CD-3 or an antigen binding fragment thereof.

27. The method according to any one of statements 21 to 26, wherein the at least one microRNA is miR-193b or miR-365.

28. The method according to any one of statements 21 to 27, wherein step (a) comprises determining the expression level of at least 2 microRNA selected from the group consisting of miR-365, miR-34a, miR-193b and miR-125a.

29. The method according to statement 28, wherein the at least two microRNA are miR-125a and one of miR-365 and miR-193b.

30. The method according to statement 28, wherein the at least two microRNA are miR-365 and miR-193b.

31. The method according to any one of statements 21 to 27, wherein step a comprises determining the level of at least 3 microRNAs selected from the group consisting of miR-365, miR-34a miR-193b or miR-125a.

32. The method according to statement 31, wherein the at least 3 microRNA are miR-365 and miR-193b and one of miR-125a or miR-34a.

33. The method according to any one of statements 21 to 32, wherein determining the expression of an miRNA comprises the step of generating cDNA form said miRNA and amplifying said cDNA.

34. The method according to any one of statements 21 to 33, wherein the therapy comprises the oral administration of a micro-organism expressing Proinsulin and Interleukin 10.

35. In vitro use of one or more oligonucleotide probes specific for the detection of at least one microRNA selected from the group consisting of miR-365, miR-34a miR-193b and miR-125a, in the prediction of the response to a therapy of proinsulin or insulin and IL-10, and an CD3 antagonist in a type 1 diabetic patient.

36. The use according to statement 35, wherein the at least one microRNA is miR-193b or miR-365.

37. The use according to statement 36, of oligonucleotide probes specific for the detection of at least two microRNA least 2 microRNA selected from the group consisting of miR-365, miR-34a, miR-193b and miR-125a.

38. The use according to statement 37, wherein the at least two microRNA is are miR-125a and one of miR-365 and miR-193b.

39. The use according to statement 37, wherein the at least two microRNA are miR-365 and miR-193b.

40. The use according to statement 36 of oligonucleotide probes specific for the detection of at least 3 microRNAs selected from the group consisting of miR-365, miR-34a miR-193b or miR-125a.

41. The use according to statement 40, wherein the at least 3 microRNA are miR-365 and miR-193b and one of miR-125a or miR-34a.

42. A kit consisting of oligonucleotide probes specific for the detection of up to 10 miRNA, characterised in that the up to 10 miRNA comprise at least two microRNA selected from the group consisting of miR-365, miR-34a miR-193b and miR-125a.

43. The kit according to statement 42, wherein the at least two micro-RNA are miR-193b and miR-365.

44. The kit according to statement 42 or 43, wherein the at least two micro-RNA are miR-193b and miR-365, and one of miR-34a or miR-125a.

45. The kit according to any one of statements 42 to 44, comprising probes for the detection of one or more exogenous or endogenous control miRNA.

46. The kit according to any one of statements 42 to 45, further comprising an exogenous control miRNA, preferably a non-human control miRNA.

47. The kit according to any of statements 42 to 46, wherein said oligonucleotide probes are specific for the detection of cDNAs obtained from said microRNAs.

48. The kit according to any one of statements 42 to 47, adapted for performance of a quantitative reverse-transcription real-time polymerase chain reaction (qRT-PCR).

The present invention analyzes the expression of circulating microRNAs in blood plasma from a longitudinally followed cohort of diabetic NOD mice treated with *L. lactis* producing human PINS and IL10 in combination with anti-CD3 in order to define one or more microRNAs for the prediction of therapy success. The identification of prognostic microRNAs in such preclinical model is of use to identify prior to therapy those T1D patients that could benefit of thereof.

BRIEF DESCRIPTION OF THE DRAWINGS

FIGS. 3A-3F are a single assay qPCR validation of microRNAs differentially expressed in the array profiling. Differentially expressed microRNAs, miR-34a (FIG. 3A)

Figures 3A, 3B, 3C:
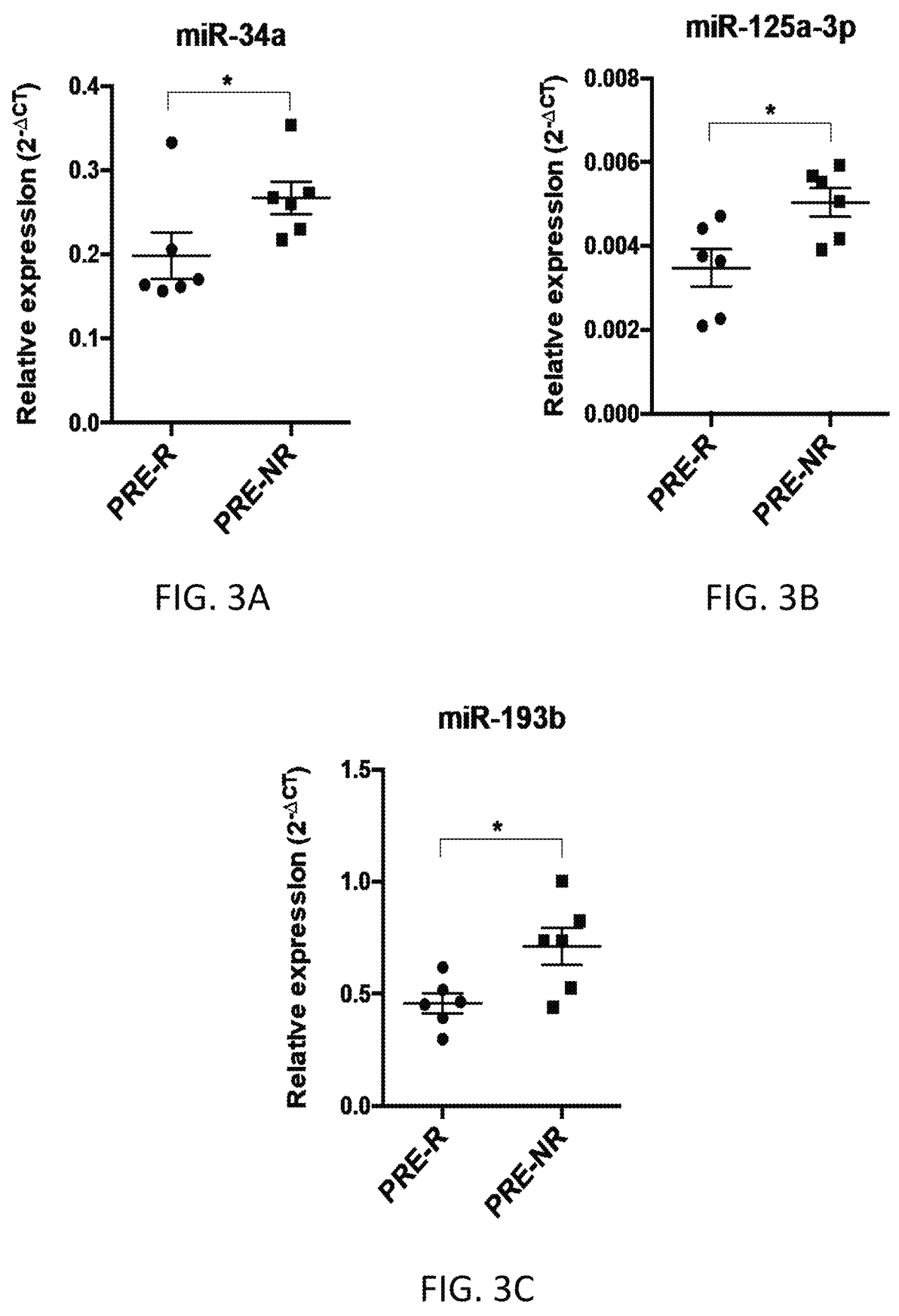
Figure 3D:
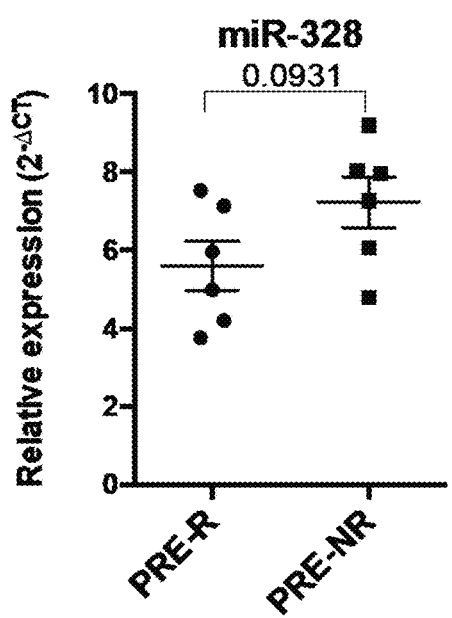
Figure 3E:
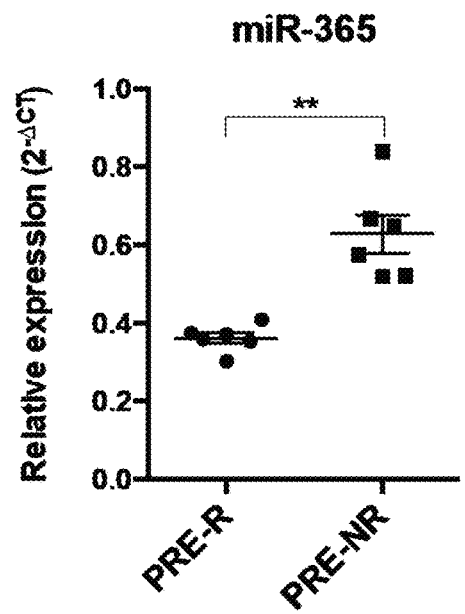
Figure 3F:
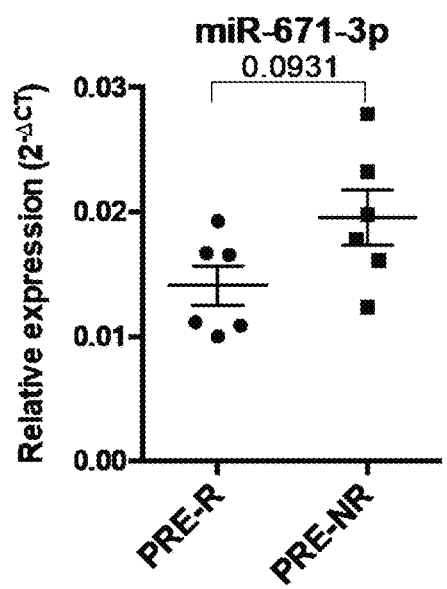
Figure 4A:
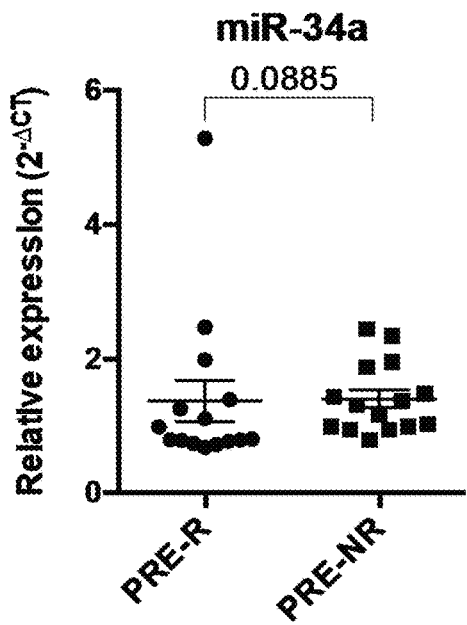
Figure 4B:
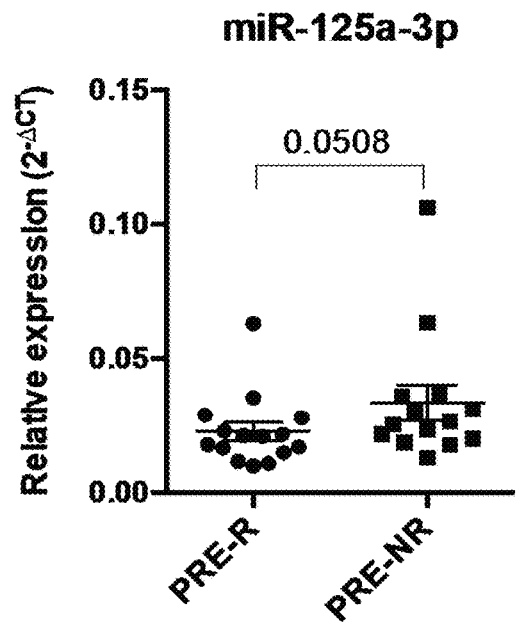
Figure 4C:
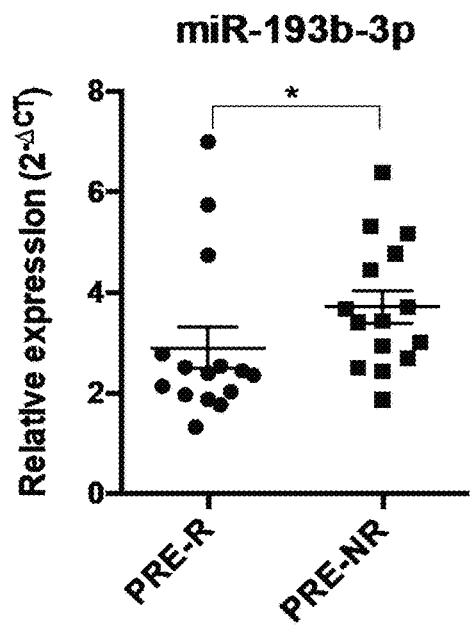
Figure 4D:
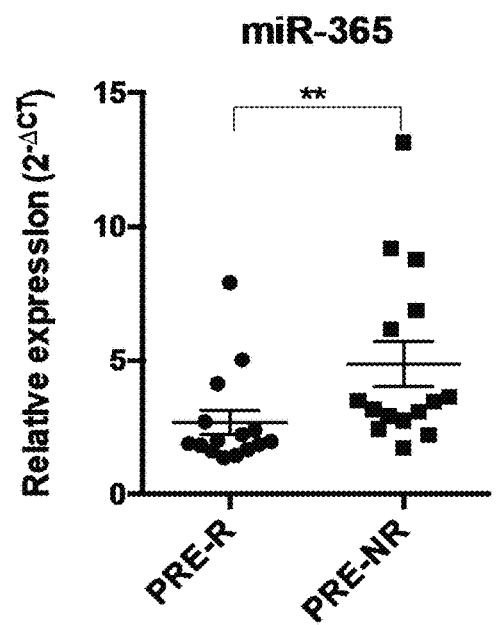

miR-125a-3p (FIG. 3B), miR-193b (FIG. 3C), miR-328 (FIG. 3D), miR-365 (FIG. 3E), miR-671-3p (FIG. 3F) were analyzed using single assay qPCR in the screening cohort samples. Data were analyzed by Mann-Whitney on $2^{-\Delta Ct}$ and are expressed as the mean±SEM. R: responders, NR: non-responders.

FIGS. 4A-4D are a differentially expressed plasma microRNAs single assay validation responder vs non-responders at disease onset in screening and validation cohorts. Differentially expressed microRNAs were validated using single assay qPCR both in the samples deriving from the screening cohort used in FIG. 3 and an additional validation cohort for a total of 15 responders and 15 non-responders plasma samples at disease onset. (FIG. 4A) miR-34a, (FIG. 4B) miR-125a-3p, (FIG. 4C) miR-193b, (FIG. 4D) miR-365 expression in plasma samples deriving from diabetic mice at diabetes onset. Data were analyzed by Mann-Whitney on $2^{-\Delta Ct}$ (ns: not significant; *p<0.05; **p<0.001) and are expressed as the mean±SEM. R: responders, NR: non-responders.

DETAILED DESCRIPTION

"Type 1 Diabetic patient" refers to subjects having one or more of the following clinical manifestations: Fasting plasma glucose level at or above 7.0 mmol/L (126 mg/dL); Plasma glucose at or above 11.1 mmol/L (200 mg/dL) two hours after a 75 g oral glucose load as in a glucose tolerance test; Symptoms of hyperglycemia and casual plasma glucose at or above 11.1 mmol/L (200 mg/dL); Glycated hemoglobin (hemoglobin A1C) at or above 48 mmol/mol (≥6.5 DCCT %).

"T1 Diabetes treatment" in the context of the present invention typically refers to the administration of at least (pro)insulin, interleukin-10 and a CD3 antagonist (such as an anti-CD3 antibody).

Insulin or proinsulin can be administered as protein in accordance with therapies and routes of administration known in the art. More typically in the context of the present invention, insulin is provided as a recombinant organism expressing insulin.

Interleukin 10 can be administered as a protein in accordance with therapies and routes of administration known in the art. More typically in the context of the present invention, IL-10 is provided as a recombinant organism expressing IL-10.

Methods of providing recombinant micro-organisms expressing therapeutic proteins are disclosed in e.g. WO2017122180. As can be appreciated, proteins with mutations, truncated versions, chimeric version and fusion proteins having therapeutic activity are equally envisaged in the context of the present invention.

(pro)Insulin and interleukin-10 are typically administered via oral administration of a micro-organism expressing recombinant proinsulin and interleukin 10.

Monoclonal antibodies against CD3 are typically used in the context of the present invention. Fragments or modified versions of antibodies or antibody binding fragments specifically binding CD3 are equally suitable.

"responder" refers to patients wherein established primary endpoint defined within the clinical trial of the mentioned treatment are fulfilled.

The experimental data obtained in the examples section has been obtained in mice. The similarity in pathology and response to the envisaged triple therapy between mice and human allows to extrapolate the data to humans and perform the claimed method on humans, using the miRNA sequences of humans if not conserved between human and mouse.

"expression level" may be determined by measuring the amount of microRNA in the sample fluid. The expression level of the microRNA can be determined, for example, with an assay for global gene expression in a biological fluid (e.g. using a microarray assay for microRNA expression profiling analysis, or a ready-to-use microRNA qPCR plate), or by specific detection assays, such as quantitative PCR, quantitative reverse-transcription (real-time) PCR (qRT-PCR), locked nucleic acid (LNA) real-time PCR, or northern blotting. The measurement of the expression level of a microRNA in a biological fluid may be carried out with an oligonucleotide probe specific for the detection of said microRNA. Said oligonucleotide probe may bind directly and specifically to the microRNA, or may specifically reverse transcribe said microRNA. Alternatively, said oligonucleotide probe may bind a cDNA obtained from said microRNA. Said oligonucleotide probe may also amplify a cDNA obtained from said microRNA.

"kit" refers to any combination of reagents or apparatus that can be used to perform a method of the invention. Kits for use in the present invention comprise probes for detection of a limited amount of dedicated miRNA (up to 10, 15 or 20 miRNA) to distinguish over arrays containing probes for more than 100 or 1000 miRNA. Apart from the miRNA as recited in the claims the dedicated miRNA may comprise housekeeping miRNA or exogenous miRNA from other species that serve as control. The kit may also comprise instructions for use to diagnose whether a subject classifies as a responder to the IL10, PINS, anti-CD3 diabetes therapy.

"oligonucleotide probe" refers to a short sequence of nucleotides that match a specific region of a microRNA or a cDNA obtained from said microRNA, or fragments thereof, and then used as a molecular probe to detect said microRNA or cDNA sequence.

An oligonucleotide probe "specific for the detection of a microRNA" for example refers to an oligonucleotide probe that bind directly and specifically to a microRNA or a fragment thereof, or specifically reverse transcribe said microRNA. Alternatively, said oligonucleotide probe may bind specifically to a cDNA obtained from said microRNA. Said oligonucleotide probe may also specifically amplify a cDNA obtained from said microRNA.

"control miRNA" refers to one or more miRNA which expression is determined using a similar, preferably identical, methodology, as the experimental miRNA. As illustrated in the examples, the expression of numerous miRNA does not differ between responders and non-responders. One or more of these miRNA can be used as internal control. Alternatively, an miRNA (e.g. a non-human) is added to a sample and acts as an external control.

Alternatively a reference is obtained by using a sample or a pool of samples from a population of validated responders or by using a sample or a pool of samples from a population of validated non-responders. Experimental data can be compared with control data and classified as belonging to the responder or non-responder group. Compared with a control group of non-responders a non-responder will have about equal expression levels, and a responder will have lower expression levels. Equally, compared with a control group of responders a responder will have about equal expression levels, and a non-responder will have higher expression levels.

General techniques useful in microRNA detection are disclosed in "MicroRNA Expression Detection Methods", Wang Zhiguo, Yang Baofeng, 2010, XX; "Circulating MicroRNAs Methods and Protocols", series: Methods in Molecular Biology, Vol. 1024 Ochiya, Takahiro (Ed.) 2013.

Determination of expression values obtained by qPCR can be expressed as 2^-dct values as explained for example in Livak & Schmittgen (2001) *Methods* 25, 402-408. This value represents the fold change in expression of the target miRNA relative to a control miRNA.

The term "statistically significant" differences between the groups studied, relates to condition when using the appropriate statistical analysis (e.g. Chi-square test, t-test) the probability of the groups being the same is less than 5%, e.g. $p<0.05$. In other words, the probability of obtaining the same results on a completely random basis is less than 5 out of 100 attempts.

Any technique known to one of skill in the art for detecting and measuring RNA expression levels can be used in accordance with the methods described herein. Non-limiting examples of such techniques include microarray analysis, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, as well as other methods.

The probe can be labelled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^{3}H$, $^{14}C$, $^{32}P$, $^{35}S$, $^{51}Cr$, $^{57}Co$, $^{58}Co$, $^{59}Fe$, $^{90}Y$, $^{125}I$, $^{131}$, and $^{186}Re$.

EXAMPLES

Example 1. Materials and Methods

Animals and Blood Drawn

NOD mice were house and inbred in animal facility of the Katholieke Universiteit Leuven (KULEUVEN, Belgium). Housing of NOD mice occurred in semi-barrier conditions, animals were fed sterile food and water ad libitum. NOD mice were screened for diabetes onset of diabetes by evaluating glucose levels in urine (Clinistix; Bayer Diagnostics, Tarrytown, NY) and venous blood (AccuChek, Roche). NOD mice were considered diabetic when having positive glycosuria and two consecutive blood glucose measurements exceeding 200 mg/dL.

New-onset diabetic NOD mice were treated for 5 consecutive days i.v. (day 0-4; 2.5 µg/mouse) with hamster anti-mouse CD3 mAb (clone 145-2C11, Bio X Cell, West Lebanon N.H.). This therapy was given alone or in combination with intragastric inoculation of *L. lactis*-PINS ($2 \times 10^9$ CFU) 5 times per week during 6 weeks. Individual glycaemia values at the start of treatment were recorded. Mice were tested 3 times weekly for their weight and blood glucose status. Remission was defined as the absence of glycosuria and return to normal [<200 mg/dL] glycaemia levels. Experimental animals were sacrificed immediately after stopping therapy, 6 weeks after treatment initiation.

Figure 1:
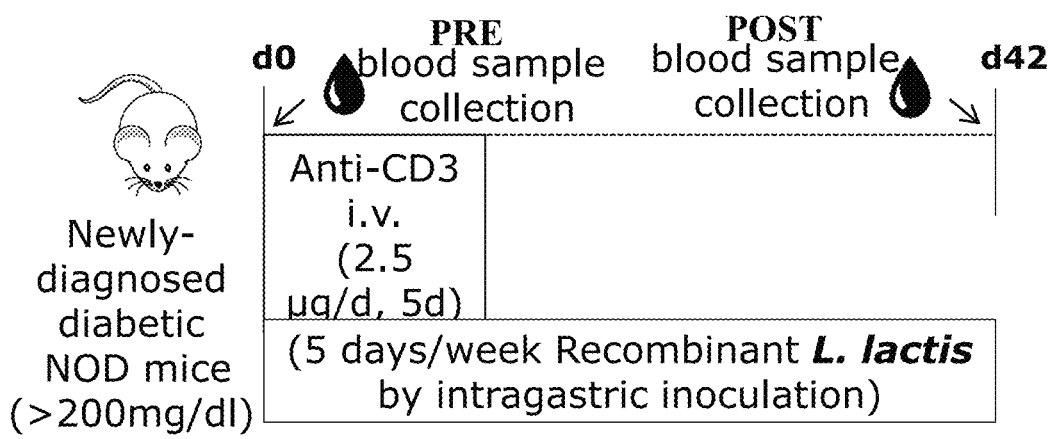
FIG. 1 is a treatment scheme and blood samples collection. Newly diagnosed diabetic NOD mice were treated with low-dose hamster anti-CD3 mAbs intravenously for 5 consecutive days with or without recombinant *L. lactis* given 5 times weekly for a period of 6 weeks (w6) by intragastric inoculation. Blood was collected at day 0 (d0; pre-therapy) and week 6 (w6; post-therapy). Weight and glycaemia were measured three times weekly. Diabetes remission was defined as the absence of glycosuria and hyperglycaemia.

Blood samples were collected from the submandibular vein in experimental animals at diabetes onset (day 0) and after 6 weeks of therapy. Blood was collected in EDTA-tubes (EDTA microvette Sarstedt 20.1288) (FIG. 1). Blood was centrifuged for 10 minutes at 2.000 g, the resulting supernatant (plasma) was collected and stored at -80° C. until further use.

Construction of *L. lactis* Expressing PINS and IL10

An *L. lactis* strain secreting human PINS, which is a major auto-Ag in T1D and the anti-inflammatory human IL10, were engineered. *L. lactis* (LL)-PINS+hIL10, was generated by transformation of the parental MG1363 strain with pThyAhPINS, a plasmid carrying PINS and hIL10 fused to the usp45 secretion signal, downstream of the PthyAlactococcal promoter.

RNA Extraction and microRNA Expression Analysis

Before RNA extraction plasma samples were thawed on ice and centrifuged again at 3.000 g for 5 min in order to remove potential cell debris. RNA was isolated starting from 50 µL of EDTA plasma by using a combination of Trizol LS and miR-Neasy minikit (Qiagen Inc.H, Germantown, MD).

Briefly, 5 volumes of Trizol LS Reagent (Life Technologies) were added to 50 µL of plasma together with 5 nM of the spike-in microRNA ath-miR-159 (Ambion). Phenol-chloroform separation followed by on-column RNA extraction was performed with Qiagen miR-Neasy Mini kit following manufacturer's instructions. Total RNA was eluted in 30 µL of nuclease-free water and then subjected to downstream reactions.

RNA samples were then processed for microRNA reverse transcription using rodent Megaplex RT-stem-loop microRNA Pool A V2.1 specific reaction that allowed the cDNA production using 384 specific microRNA primers. Each reverse transcription reaction was made of: -0.8 µL Megaplex rodent RT stem-loop primers PoolA v2.1 (10x), 0.2 µL dNTPs (100 mM), 1.5 µL Multiscribe RT 50 U/µL, 0.8 µL 10x RT buffer, 0.9 µL $MgCl_2$ (25 mM), 0.1 µL RNAse Inhibitor 20 U/µL, 0.2 µL Nuclease free water and 2 µL RNA from extracted from plasma sample. The reaction underwent the following temperatures and cycles: 40 cycles (16° C.x2 min, 42° C.x1 min, 50° C.x1 sec), 85° C.x5 min.

The resulting cDNA was then subjected to specific pre-amplification reaction in order to enhance expression output using specific primers. Each reaction was composed of: 12.5 µL Taqman preamp Master Mix 2x, 2.5 µL Megaplex microRNA Rodent Preamp Primers Pool A v2.1, 2.5 µL of multiplex microRNAs RT reaction and 7.5 µL Nuclease free water. The reaction underwent the following temperatures and cycles: 95° C.x10 min, 55° C.x2 min, 72° C.x2 min, 12 cycles (95° C.x15 sec, 60° C.x4 min), 99.9° C.x10 min. Preamp products were diluted by adding 75 µL of 0.1x Tris-EDTA pH 8.0. Pre-amplified cDNA was then stored at -20° C. before performing quantitative Real-Time reaction (qPCR). Taqman Array Rodent microRNA cards (Panel A v2.1) were used in order to evaluate the expression of 384 microRNAs. The microRNA array card is made of 8 ports through which the TaqMan Universal PCR Master Mix containing the sample is loaded. The reaction mix was composed of: 450 µL Taqman Universal PCR Master Mix II 2x, 350 µL Nuclease free water and 100 µL of specific pre-amplified cDNA.

Each port of Taqman array cards was loaded with 100 µL reaction mix. The microRNA array card was then centrifuged twice at 1200 rpm for 1 min. RT-qPCR was set at the following temperature and cycles: 95° C.×10 min, 40 cycles (95° C.×15 sec, 60° C.×1 min).

For the following selected microRNA, single assay evaluation using TaqMan microRNA single assay qPCR using pre-amplified product was performed: miR-34a (ID000426), miR-125a-3p (ID002199), miR-193b (ID002467), miR-328 (ID000543), miR-365 (ID001020), miR-671-3p (ID002322). MicroRNA mature sequences are reported in table 1. ID numbers refer to primer accession numbers of ThermoFisher.

The reaction for microRNAs single assay qPCR was composed of: 10 μL Taqman Universal PCR Master Mix II 2×, 1 μL MicroRNAs Single Assay Primers 20×, 6.5 μL Nuclease free water and 2.5 μL preamplified cDNA previously diluted 1:40 in TE buffer. Temperatures and cycles were the same applied to perform the microRNAs profiling. All the reagents were from Life Technologies. The RT and pre-amplification reactions were performed on Veriti Thermal cycler and the TaqMan Array cards and qPCR single assay evaluation using ViiA7® instrument (all from Life Technologies).

Receiving operating characteristic (ROC) analysis were employed in order to identify the microRNAs with better ability to predict responders vs non-responders mice groups and derive a group of predictive microRNAs based on specificity and sensitivity. Graphs and ROC curves were generated with GraphPad Prism.

Example 2. miRNA Expression Profiling microRNA expression analysis of plasma samples collected at diabetes onset was performed in order to investigate whether stratifying the samples at study entry for their final therapeutic outcome, namely responders and non-responders, could possibly lead to the identification of a set of circulating microRNAs that could predict therapeutic success.

The expression profiles of 384 microRNAs were analysed starting from total RNA extracted from 50 μL of EDTA plasma from newly diagnosed diabetic mice before L. lactis therapy. By comparing the resulting circulating microRNA expression profiles of responders (n=6) and non-responders

TABLE 1

MicroRNA sequences

| miRNA name | miR-base Acc. ID | Location Chromosome (on Build v38) | Mature sequence (5'-3') | Conserved Sequence Mouse/ Human |
|---|---|---|---|---|
| mmu-miR-34a-5p | MIMAT 0000542 | Chr. 4 150068454-150068555 [+] | UGGCAGUGUCUUAG CUGGUUGU [SEQ ID NO: 1] | Yes |
| mmu-miR-125a-3p | MIMAT 0004528 | Chr. 17 17830812-17830879 [+] | ACAGGUGAGGUUCU UGGGAGCC [SEQ ID NO: 2] | Yes |
| mmu-miR-193b-3p | MIMAT 0004859 | Chr. 16 13449523-13449601 [+] | AACUGGCCCACAAA GUCCCGCU [SEQ ID NO: 3] | No |
| mmu-miR-328-3p | MIMAT 0000752 | Chr. 16 67202321-67202395 [-] | CUGGCCCUCUCUGCC CUUCCGU [SEQ ID NO: 4] | Yes |
| mmu-miR-365-3p | MIMAT 0000711 | Chr. 11 79726400-79726511 [+] Chr. 16 13453840-13453926 [+] | UAAUGCCCCUAAAA AUCCUUAU [SEQ ID NO: 5] | Yes |
| mmu-miR-671-3p | MIMAT 0004821 | Chr. 5 24592114-24592211 [+] | UCCGGUUCUCAGGG CUCCACC [SEQ ID NO: 6] | Yes |

Data Analysis

Results were collected and exported using VIIA7 RUO Software v2.1 and analyzed by Expression Suites Software v1.0,3, through the $2^{-ddCt}$ or $2^{-dCT}$ method, differentially expressed microRNAs were identified using Mann-Whitney test on $2^{-dct}$.

The measurement of the expression level of each microRNA is reported as Cycles to Threshold (Ct) of PCR, a relative value that represents the cycle number at which the amount of amplified DNA reaches the threshold level. Because of the possible technical variability between experiments the Ct were normalized (dCt) using endogenous controls retrieved by the algorithm NormFinder (mmu-miR-30d, mmu-miR-744, ath-miR-159). Endogenous controls were therefore chosen based on their stability value (M-value) as the lowest among a wider set of candidates.

(n=6) before therapy initiation, a pattern of differentially expressed microRNAs was obtained potentially linked to the final therapeutic outcome. In order to avoid any confounding factors, the plasma samples selected for the microRNA profiling were matched for age, sex and disease aggressiveness at onset determined by starting glycaemic levels between the two study groups. In order to identify plasma circulating microRNAs differentially expressed between responder and non-responders mice at disease onset, microRNA expression data were normalized using a combination of a spike-in exogenous synthetic microRNA (ath-miR-159a) and two endogenous microRNAs (miR-744 and miR-30d) which resulted as the most stable microRNAs from the dataset.

Figure 2:
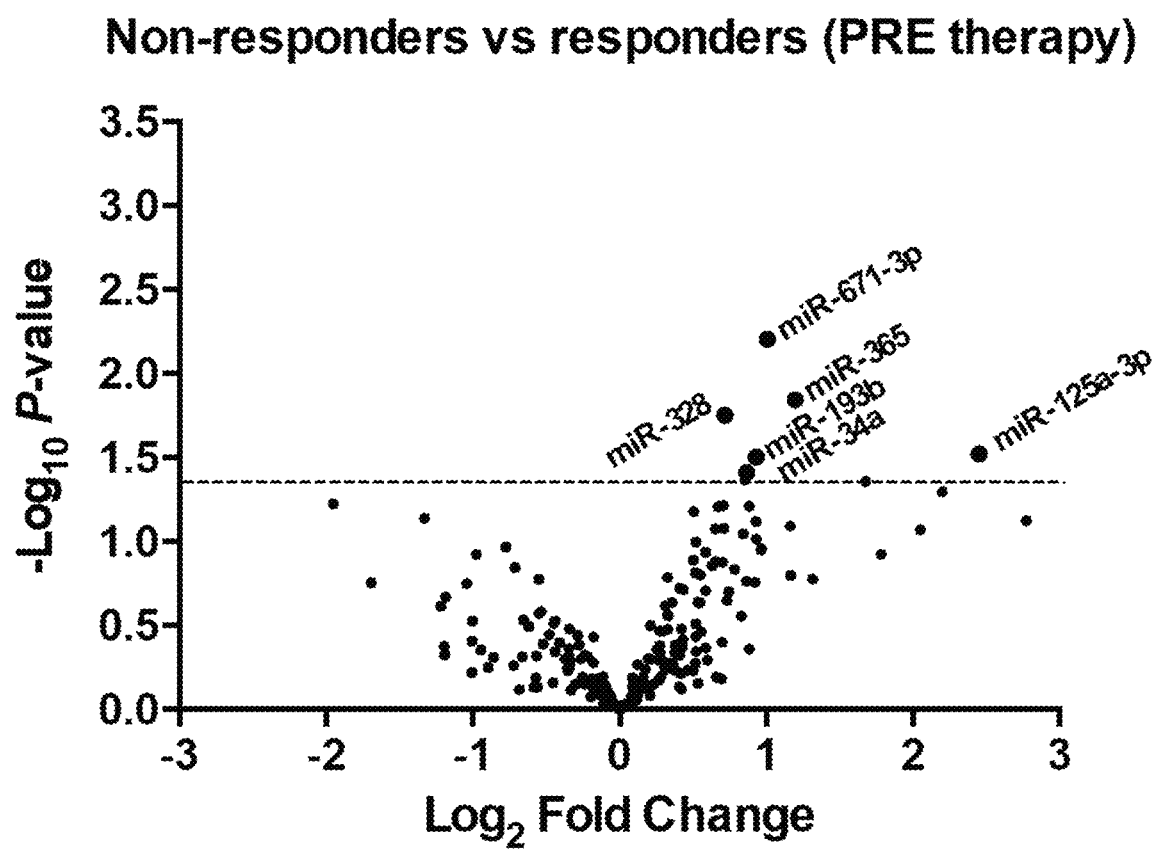
FIG. 2 illustrates microRNA profiling in responder and non-responder mice before therapy. Volcano plot analysis showing the differential expression of plasmatic microRNAs in NOD non-responder mice vs. responder NOD mice at diabetes onset. The log-transformed values of fold change are reported on the x-axis while $-\log_{10}$ transformed values of the p-value are shown on the y-axis. Cut-off thresholds of the p-value (Student t test p<0.05) threshold is depicted by the dotted line. Dots above the line depict samples significantly differentially expressed with student-t-test and Mann-Whitney. Differentially expressed microRNAs are indicated in the upper-right area of the volcano plot.

Volcano plot analysis revealed a total of 6 microRNAs (miR-34a, miR-125a-3p, miR-193b, miR-328, miR-365, miR-671-3p) specifically upregulated at diabetes onset in non-responders vs. responders, while no microRNA were statistically downregulated (FIG. 2).

Example 3. miRNA Expression of Responders and Non-Responders to IL-10 PINS Therapy Individual qPCR assay validation in the same cohort of samples previously screened with the profiling was performed. Single assay experiments validated the specific upregulation of miR-34a (FIG. 3A), miR-125a-3p (FIG. 3B), miR-193b (FIG. 3C) and miR-365 (FIG. 3E) in non-responders vs. responder mice at disease onset. The increased expression of miR-328 (FIG. 3D) and miR-671-3p (FIG. 3F) in non-responders vs. responder mice at disease onset was not statistically significant.

The identification and technical validation of a specific prognostic microRNA signature of 4 microRNAs differentially expressed at disease onset prompted us to validate this finding using single assay qPCR in an additional validation cohort in order to reach 15 plasma samples per group.

Single assay experiments in a larger cohort validated the specific upregulation of miR-34a (FIG. 4A), miR-125a-3p (FIG. 4B), miR-193b (FIG. 4C) and miR-365 (FIG. 4D) in non-responders vs. responder mice at disease onset. The sensitivity and specificity of the microRNAs was validated through qPCR by generating receiver ROC curves with these two different cut-offs (Table 2). ROC curves plot sensitivity against the specificity for the different possible cut-off of a diagnostic test, and the area under the ROC curves shows the accuracy of the test, separating groups tested into those that will benefit or not from the therapy. An area under the curve (AUC) of 1 indicates that the test is perfectly accurate to distinguish between the mice that will respond or not to the therapy, whereas an area of 0.5 indicates that the test fails to distinguish the two groups (Table 2).

TABLE 2

Receiver-operating characteristic curves values generated by single or multiple microRNA combination analysis

| microRNA | Sensitivity (%) | Specificity (%) | AUC | p-value |
|---|---|---|---|---|
| miR-34a | 80 | 60 | 0.68 | 0.08 |
| miR-125a | 64.29 | 73.33 | 0.71 | 0.049 |
| miR-193b | 73.33 | 80 | 0.74 | 0.02 |
| miR-365 | 80 | 80 | 0.80 | 0.004 |
| miR-34a + miR-193b | 80 | 60 | 0.72 | 0.03 |
| miR-34a + miR-125a | 78.57 | 60 | 0.68 | 0.09 |
| miR-34a + miR-365 | 86.67 | 66.67 | 0.77 | 0.01 |
| miR-125a + miR-193b | 78.57 | 73.33 | 0.73 | 0.03 |
| miR-125a + miR-365 | 85.71 | 73.33 | 0.79 | 0.006 |
| miR-193b + miR-365 | 86 | 80 | 0.79 | 0.006 |
| miR-34a + miR-193b + miR-365 | 73.33 | 80 | 0.77 | 0.01 |
| miR-34a + miR-125a miR-193b | 71.43 | 66.67 | 0.70 | 0.05 |
| miR-34a + miR-125a miR-365 | 85.71 | 66.67 | 0.76 | 0.01 |
| miR-125a + miR-193b + miR-365 | 85.71 | 80 | 0.78 | 0.01 |
| miR-34a + miR-125a + miR-193b + miR-365 | 85.71 | 66.67 | 0.76 | 0.01 |

The invention claimed is:

1. An in vitro method for identifying a type 1 diabetic patient as a responder to a combination therapy, the combination therapy comprising administering to the diabetic patient (1) Proinsulin or insulin, and (2) Interleukin 10, and (3) a CD3 antagonist, the method comprising:
 (a) determining the expression level of at least one microRNA (miRNA), selected from the group consisting of miR-365, miR-34a, miR-193b, and miR-125a, in a sample from the diabetic patient prior to receiving the combination therapy;
 (b) comparing the expression level as determined in (a) with a control;
 (c) determining from the comparison, whether the diabetic patient is a responder to the combination therapy; and
 (d) treating the responder with the combination therapy.

2. The method according to claim 1, further comprising normalizing expression levels determined in (a) against the expression of one or more control miRNA.

3. The method according to claim 1, wherein the control is one more endogenous miRNA.

4. The method according to claim 1, wherein a low expression level of said at least one miRNA in the sample compared to the one or more control miRNA is indicative for a responder to the combination therapy.

5. The method according to claim 1, wherein the control is the expression level of the at least one miRNA in one or more responder control persons.

6. The method according to claim 1, wherein the CD-3 antagonist is an antibody against CD-3 or an antigen binding fragment thereof.

7. The method according to claim 1, wherein the at least one miRNA is miR-193b or miR-365.

8. The method according to claim 1, wherein (a) comprises determining the expression level of at least two miRNAs selected from the group consisting of miR-365, miR-34a, miR-193b and miR-125a.

9. The method according to claim 8, wherein the at least two miRNAs are miR-125a and one of miR-365 and miR-193b.

10. The method according to claim 8, wherein the at least two microRNA miRNAs are miR-365 and miR-193b.

11. The method according to claim 1, wherein (a) comprises determining the level of at least three miRNAs selected from the group consisting of miR-365, miR-34a, miR-193b and miR-125a.

12. The method according to claim 11, wherein the at least three miRNAs are miR-365 and miR-193b and one of miR-125a or miR-34a.

13. The method according to claim 1, wherein determining the expression of an miRNA comprises generating cDNA from said miRNA and amplifying said CDNA.

14. The method according to claim 1, wherein the combination therapy comprises orally administering to the diabetic patient a micro-organism that expresses Proinsulin and Interleukin 10.

* * * * *

UNITED STATES PATENT AND TRADEMARK OFFICE
CERTIFICATE OF CORRECTION

| | | |
|---|---|---|
| PATENT NO. | : 12,139,761 B2 | Page 1 of 1 |
| APPLICATION NO. | : 17/043136 | |
| DATED | : November 12, 2024 | |
| INVENTOR(S) | : Constantia Gysemans et al. | |

It is certified that error appears in the above-identified patent and that said Letters Patent is hereby corrected as shown below:

In the Specification

In Column 2, Line(s) 34, delete "least 2 microRNA".

In Column 3, Line(s) 63, delete "least 2 microRNA".

In Column 3, Line(s) 66, after "microRNA", delete "is".

In Column 4, Line(s) 39, after "benefit", delete "of".

In Column 7, Line(s) 40, delete "59Fe," and insert --$^{59}$Fe,--, therefor.

In the Claims

In Column 14, Line(s) 57, Claim 10, before "miRNAs", delete "microRNA".

In Column 14, Line(s) 67, Claim 13, delete "CDNA" and insert --cDNA--, therefor.

Signed and Sealed this
Twentieth Day of May, 2025

Coke Morgan Stewart
*Acting Director of the United States Patent and Trademark Office*

SEQUENCE LISTING

```
<160> NUMBER OF SEQ ID NOS: 6

<210> SEQ ID NO 1
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miR-34a

<400> SEQUENCE: 1
uggcaguguc uuagcugguu gu                                              22

<210> SEQ ID NO 2
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miR-125a

<400> SEQUENCE: 2
acaggugagg uucuugggag cc                                              22

<210> SEQ ID NO 3
<211> LENGTH: 22
<212> TYPE: RNA
<213> ORGANISM: Mus musculus
<220> FEATURE:
<221> NAME/KEY: misc_feature
<222> LOCATION: (1)..(22)
<223> OTHER INFORMATION: miR-193b
```

```
<400> SEQUENCE: 3
aacuggccca caaagucccg cu                                          22

<210> SEQ ID NO 4
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miR-328

<400> SEQUENCE: 4
cuggcccucu cugcccuucc gu                                          22

<210> SEQ ID NO 5
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miR-365

<400> SEQUENCE: 5 uaaugcccu aaaaauccuu au                                           22

<210> SEQ ID NO 6
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: 617

<400> SEQUENCE: 6
uccgguucuc agggcuccac c                                           21
```